United States Patent [19]

Hiraishi et al.

[11] Patent Number: 6,048,519
[45] Date of Patent: *Apr. 11, 2000

[54] HAIR TREATMENT COMPOSITIONS

[75] Inventors: Takahiro Hiraishi; Kyoko Matsumoto, both of Tochigi-ken, Japan; Andrew Malcolm Murray, Bebington, United Kingdom; Tadashi Numata, Tochigi-ken, Japan

[73] Assignee: Helene Curtis, Inc., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/047,281

[22] Filed: Mar. 24, 1998

[30] Foreign Application Priority Data

Mar. 27, 1997 [GB] United Kingdom .................. 9706486

[51] Int. Cl.⁷ .................................................. A61K 7/075
[52] U.S. Cl. .................. 424/70.122; 424/70.12; 424/70.121
[58] Field of Search ........................... 424/70.12, 70.122, 424/70.121

[56] References Cited

U.S. PATENT DOCUMENTS 3,958,581  5/1976  Abegg et al. ............................. 132/7
3,962,418  6/1976  Birkofer .................................... 424/70
4,009,256  2/1977  Nowak, Jr. et al. ...................... 424/70
4,806,338  2/1989  Smith .
5,100,657  3/1992  Ansher-Jackson ........................ 424/70
5,180,584  1/1993  Sebag et al. .
5,567,428  10/1996  Hughes .................................... 424/401
5,618,524  4/1997  Bolich .................................. 424/70.12
5,710,113  1/1998  Wells ..................................... 510/122

FOREIGN PATENT DOCUMENTS

92/10162  6/1992  WIPO .
95/22311  8/1995  WIPO .

OTHER PUBLICATIONS

International Search Report No. PCT/EP 98/01768 completed Sep. 3, 1998.

*Primary Examiner*—Jyothsna Venkat
*Attorney, Agent, or Firm*—Matthew Boxer

[57] ABSTRACT

A hair treatment composition, such as a shampoo or conditioner, which comprises a silicone component which comprises a silicone gum with a viscosity greater than 1 Mcs, a silicone fluid with a viscosity of less than 100 kcs, and an amino functionalised silicone.

2 Claims, No Drawings

6,048,519

HAIR TREATMENT COMPOSITIONS

FIELD OF THE INVENTION

This invention relates to hair treatment compositions containing particular types of silicones, which can provide the composition with conditioning benefits.

BACKGROUND AND PRIOR ART

The use of silicones as conditioning agents in hair treatment compositions is well known, and widely documented in the patent literature.

We have surprisingly found that a particular combination of silicone compounds can be used in hair treatment compositions to provide excellent conditioning benefits.

SUMMARY OF THE INVENTION

In a first aspect, the present invention provides a hair treatment composition comprising a silicone component which comprises a silicone gum with a viscosity greater than 1 Mcs, a silicone fluid with a viscosity of less than 100 kcs, and an amino functionalised silicone.

DETAILED DESCRIPTION AND PREFERRED EMBODIMENTS (i) Silicone Component

Preferably, the total silicone content of the composition of the invention is in the region of 0.1 to 20%, based on the total weight of the composition.

Suitably, the silicone gum of viscosity greater than 1 Mcs comprises less than 50% by weight, the silicone fluid of viscosity less than 100 kcs comprises greater than 30% by weight, and the amino functionalised silicone comprises less than 10% by weight, based on the total silicone content of the silicone component of the composition.

In a highly preferred aspect of the invention, the silicone component of the composition may be provided as a single blend, which may be added to the composition during manufacture. This single blend may simply be in the form of a silicone mixture which can be added to the composition during manufacture, or it may be in an alternative form such as an aqueous emulsion which may itself be added to the composition during manufacture. Pre-formed aqueous emulsions of silicone may have advantages in that they themselves may be easier to handle or process than the "raw" silicone ingredients of the silicone component.

In any event, when added to the hair treatment composition, the silicone component becomes the internal phase of an emulsion which itself constitutes the hair treatment composition, and which is preferably water based.

A further feature of the invention is that the silicone present in the composition, when added as an already homogenised mixture, will be present in the hair treatment composition as a homogeneous mixture of silicones. That is, each silicone droplet in the composition will have essentially the same composition and will comprise a mixture (typically a solution) of the three types of silicone which together make up the silicone component of the composition, i.e silicone gum, silicone fluid and amino functionalised silicone.

The silicone component of the composition of the invention comprises three types of silicone, which may broadly be stated as being a silicone gum, a silicone fluid, and an amino functionalised silicone. These three types of silicone may be further characterised as follows.

Silicone Gum

The silicone gum is typically present in the silicone component at a level of from 0.01 to 50%, preferably from 1 to 40%, ideally from 10 to 35% by weight based on the total weight of the silicone component.

Preferred silicone gums are polydiorganosiloxanes, preferably derived from suitable combinations of $R_3SiO_{0.5}$ and $R_2SiO$ units, where each R independently represents an alkyl, alkenyl (e.g. vinyl), alkaryl, aralkyl or aryl (e.g. phenyl) group. R is most preferably methyl.

The silicone gum has a viscosity of greater than 1 Mcs. The viscosity can be measured by means of a glass capillary viscometer as set out further in Dow Corning Corporate Test Method CTM004, Jul. 20 1970.

Preferred silicone gums for use in the silicone component of compositions of the invention are polydimethylsiloxanes (which have the CTFA designation dimethicone), optionally having end groups such as hydroxyl. Good results have been obtained with dimethicone. Suitable materials include gums SE30, SE54 and SE76, available from General Electric Silicones.

Silicone Fluid

A further ingredient of the silicone component of the composition of the invention is a silicone fluid.

The silicone fluid is typically present in the silicone component at a level of from 30 to 95%, preferably from 40 to 80%, ideally from 50 to 70% by weight based on the total weight of the silicone component.

Preferred silicone fluids are polydiorganosiloxanes, preferably also derived from suitable combinations of $R_3SiO_{0.5}$ and $R_2SiO$ units, where each R independently represents an alkyl, alkenyl (e.g. vinyl), alkaryl, aralkyl or aryl (e.g. phenyl) group. R is most preferably methyl.

The silicone fluid has a viscosity of less than 100 kcs. The viscosity can be measured by means of a glass capillary viscometer as described above under "Silicone Gum".

Preferred silicone fluids for use in the silicone component of compositions of the invention are polydimethylsiloxanes (which have the CTFA designation dimethicone), optionally having end groups such as hydroxyl. Good results have been obtained with dimethicone. Suitable materials include the DC200 series of silicone fluids, available from Dow Corning (e.g. DC200, viscosity 350 cst), or SF96 or the VISCASIL series of silicones, available from General Electric Silicones.

A further contemplated embodiment of the invention is that the silicone gum and silicone fluid may be sourced as a single pre-prepared solution. Such solutions may themselves have benefits in terms of ease of handling. Examples of such pre-prepared blends include Q2-1403 available from Dow Corning, or CF 1251, available from General Electric Silicones.

Amino functionalised silicone

The third ingredient of the silicone component of the composition is an amino functionalised silicone.

The amino functionalised silicone is typically present in the silicone component at a level of from 0.1 to 10%, preferably from 1 to 10% by weight based on the total weight of the silicone component.

It is preferred that the amino functionalised silicone comprises no more than 10% by weight of the silicone component, firstly in order to minimise the cost of the silicone component, but also to ease emulsification of the silicone component.

Suitable amino functionalised silicones are described in EP 455,185. Suitable amino functionalised silicones include trimethylsilylamodimethicone as depicted below, and are sufficiently water insoluble so as to be useful in compositions of the invention:

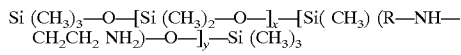

wherein x+y is a number from about 50 to about 500, and the mole % amine functionality is in the range of from about 0.7 to about 8%, and wherein R is an alkylene group having from 2 to 5 carbon atoms. Preferably, the number x+y is in the range of from about 100 to about 300, and the mole % amine functionality is in the range of from about 2 to about 6%.

Examples of amino functionalised silicones useful in the silicone component of the composition of the invention are Q2-8220 and Q2-8466 fluids, available from Dow Corning, and also SF-1708-D1, available from General Electric Silicones.

As described above, it is a highly preferred aspect that the silicone component of the composition is provided as a single blend, which may be added to the composition during manufacture. This single blend may simply be in the form of a silicone mixture which can be added to the composition during manufacture, or it may be in an alternative form such as an aqueous emulsion which may itself be added to the composition during manufacture.

An aqueous emulsion is the preferred form for such a single blend, most preferably a mechanically-formed aqueous emulsion. In such emulsions, it is highly preferable that the emulsion additionally includes at least one emulsifier in order to stabilise the silicone emulsion.

Suitable emulsifiers are well known in the art and include anionic and nonionic surfactants. Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic surfactants used as emulsifiers for the silicone particles are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Preferably, the average particle size of the silicone droplets in the emulsion and also in the final composition is less than 20 microns, more preferably less than 10 microns. A smaller silicone particle size enables a more uniform distribution of silicone on the hair for the same amount of silicone in the composition.

Silicone particle size may be measured by means of a laser light scattering technique, for example using a 2600D Particle Sizer from Malvern Instruments.

A particularly suitable emulsion for use as the silicone component of the composition of the invention is a preformed emulsion containing silicone gum, silicone fluid and an amino functionalised silicone in a nonionic surfactant base, of silicone particle size 5 microns.

Hair treatment compositions according to the invention may suitably take the form of shampoos, conditioners, sprays, mousses or lotions. Preferred hair treatment composition forms are shampoos, conditioners and mousses.

(ii) Shampoo Compositions

A particularly preferred hair treatment composition in accordance with the invention is a shampoo composition.

Cleansing Surfactant

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit. Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO-(G)$_n$ wherein R is a branched or straight chain alkyl group which may be saturated or unsaturated and G is a saccharide group.

R may represent a mean alkyl chain length of from about C$_5$ to about C$_{20}$. Preferably R represents a mean alkyl chain length of from about C$_8$ to about C$_{12}$. Most preferably the value of R lies between about 9.5 and about 10.5. G may be selected from C$_5$ or C$_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifier for the silicone component) in shampoo compositions of the invention is generally from 0.1 to 50% by weight, preferably from 5 to 30%, more preferably from 10% to 25% by weight of the total shampoo composition.

Cationic Deposition Polymer

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides (as described in WO95/22311).

Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

A—O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

(iii) Conditioners

Compositions in accordance with the invention may also be formulated as conditioners for the treatment of hair (typically after shampooing) and subsequent rinsing.

Conditioning Surfactant

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

In conditioners of the invention, the level of cationic surfactant is preferably from 0.01 to 10%, more preferably 0.05 to 5%, most preferably 0.1 to 2% by weight of the composition.

Fatty Alcohol

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

(iv) Mousses

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from about 3% to about 30%, preferably from about 5% to about 15% of the total composition.

Small quantities of surfactant ranging anywhere from 0.1 to about 10%, preferably from about 0.1 to about 1%, most preferably about 0.3% by weight may be present in the hair mousse compositions of the invention. The surfactant may be an anionic, nonionic or cationic emulsifier. Particularly preferred are nonionic emulsifiers which are formed from alkoxylation of hydrophobes such as fatty alcohols, fatty acids and phenols.

(v) Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Mode of Use

The compositions of the invention are primarily intended for topical application to the hair and/or scalp of a human subject to improve hair fibre surface properties such as smoothness, softness, manageability, cuticle integrity, and shine.

The invention will now be further illustrated by the following, non-limiting Examples:

EXAMPLES

Example 1

A shampoo composition was prepared by mixing the following components in the amounts stated

| Component | % by weight |
| --- | --- |
| Sodium lauryl ether sulphate 2EO | 14.0 |
| Cocamidopropyl betaine | 2.0 |
| JAGUAR C13S | 0.2 |
| CARBOPOL 980 | 0.4 |
| Silicone[1] | 3.3 |
| Preservative, colour, fragrance | q.s. |
| Water | to 100% |

[1] A 50% emulsion of silicone gum/silicone, fluid, and amino functionalised silicone

Example 2

A shampoo composition was prepared by mixing the following components in the amounts stated.

| Component | % by weight |
| --- | --- |
| Sodium lauryl ether sulphate 2EO | 8.0 |
| Cocamidopropyl betaine | 4.0 |
| JAGUAR C13S | 0.1 |
| EUPERLAN PK3000[2] | 8.0 |
| Silicone[3] | 3.3 |
| Preservative, colour, fragrance | q.s. |
| Water | to 100 |

[2] Mixture of SLES 4E0, glycol distearate pearlizer and cocamidopropyl betaine, ex. Henkel.
[3] Mixture of silicone 30% SE30 (ex GE Silicones), 65% silicone DC200 (350cs) (ex Dow Corning) and 5% Q2-8220 (ex Dow Corning)

Example 3

A hair conditioning composition was prepared by mixing the following components in the amounts stated.

| Component | % by weight |
| --- | --- |
| Cetyl trimethylammonium chloride | 0.7 |
| Cetostearyl alcohol | 1.2 |
| Glyceryl monostearate | 0.7 |
| Paraffin wax | 1.0 |
| Silicone[1] | 3.3 |
| Preservative, colour, fragrance | q.s. |
| Water | to 100% |

Example 4

A hair mousse was prepared by mixing the following components in the amounts stated.

| Component | % by weight |
| --- | --- |
| Silicone[3] | 1.0 |
| EMPILAN NP9[4] | 0.3 |
| Butane/propane | 5.5 |
| Preservative, fragrance | q.s. |
| Water | to 100 |

[4] Nonyl phenol ethoxylate 9EO, ex Albright & Wilson

Example 5

The following conditioner compositions were prepared:

| | FORMULATION: | | |
| --- | --- | --- | --- |
| | A | B | C |
| Ingredient | % by weight | | |
| Cetyl trimethyl ammonium chloride | 0.9 | 0.9 | 0.9 |
| Stearyl alcohol | 2.3 | 2.3 | 2.3 |
| Cetyl Palmitate | 0.5 | 0.5 | 0.5 |
| Paraffin Wax | 1.0 | 1.0 | 1.0 |
| Perfume & minor ingredients | qs | qs | qs |
| Silicone Emulsion A[5] | 4.0 | — | — |
| Silicone Emulsion B[6] | — | 3.3 | — |
| Silicone Emulsion C[7] | — | — | 3.3 |
| Water | to 100 | to 100 | to 100 |

[5] Silicone Emulsion A is a mechanical emulsion of 60 kcs silicone fluid with a silicone activity of 50%.
[6] Silicone Emulsion B is a mechanical emulsion of silicone gum/fluid/aminosilicone with a ratio of 4:6:1, with a silicone activity of 60%.
[7] Silicone Emuslion C is a mechanical emulsion of silicone gum/fluid with a ratio of 4:6 with a silicone activity of 60%.

Conditioning Performance

The condition of hair switches after washing in the conditioners described in Example 5 was measured by wet smoothness and dry combing as follows.

10 g of hair in the form of a switch was worked in 1.0 g of a non-conditioning shampoo, lathered for 30 seconds, and rinsed with water. The switches were then washed with 1 g of conditioner for 1 minute and rinsed with water. The procedure was repeated once. Three switches of hair were prepared for each product to be evaluated. The evaluation of wet smoothness and dry combing was carried out by twelve trained panellists as a paired comparison test and significant differences at greater than 95% confidence were assessed. For wet smoothness evaluations the hair was kept damp between evaluations by spraying with water. The smoothness of each switch was assessed by the experts using their non-writing hand.

Results are shown in the following table, with each row including entries for two conditioners being compared in the form of relative allocation of a total score of 100, a higher score indicating preference for that member of the pair.

Results

| | Votes for A(%) | |
| --- | --- | --- |
| | Wet Smoothness | Dry Combing |
| A vs B | 24%* | 4%* |
| A vs C | 43% (ns) | 6%* |

*-significantly worse at $p < 0.05$
ns-no significant difference

The results show that the gum/fluid mix can give improved dry conditioning over the control, but the combination of three silicones (i.e. fluid/gum/amino functionalised silicone) can provide benefits with regard to both wet and dry conditioning.

We claim:

1. A hair treatment composition comprising a silicone component which is a homogeneous mixture of silicones comprising:

0.01 to 50% by weight based on total weight of the silicone component of a silicone gum with a viscosity greater than 1 Mcs;

30 to 95% by weight based on the total weight of the silicone component of a silicone fluid with a viscosity of less than 100 kcs;

0.1 to 10% by weight based on total weight of the silicone component of an amino functionalized silicone of the formula:

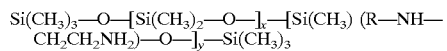

wherein x+y is a number from about 50 to about 500, and the mole % amine functionality is in the range of from about 0.7 to about 8%, and wherein R is an alkylene group having from 2 to 5 carbon atoms; and 10 to 25% by weight of the total shampoo composition of a cleansing surfactant selected from the group consisting of anionic, amphoteric and zwitterionic surfactants, and mixtures thereof.

2. A composition in accordance with claim 1, wherein the number x+y is in range of from about 100 to 300, and the mole % amine functionality is in the range of from about 2 to about 6%.

* * * * *